United States Patent [19]
Brancato

[11] Patent Number: 5,458,636
[45] Date of Patent: Oct. 17, 1995

[54] PROSTHETIC DEVICE FOR REPAIR AND REPLACEMENT OF FIBROUS CONNECTIVE TISSUE

[75] Inventor: Donald H. Brancato, St. Louis, Mo.

[73] Assignee: U.S. Biomaterials Corporation, Baltimore, Md.

[21] Appl. No.: 277,840

[22] Filed: Jul. 20, 1994

[51] Int. Cl.[6] .................................................. A61F 2/02
[52] U.S. Cl. .............................. 623/11; 623/1; 623/13; 606/151
[58] Field of Search ................................ 623/11, 13, 1; 606/151, 154; 600/37

[56] References Cited

U.S. PATENT DOCUMENTS

| | | | |
|---|---|---|---|
| 3,272,204 | 9/1966 | Artandi et al. | 606/151 |
| 3,463,158 | 8/1969 | Schmitt et al. | 606/154 |
| 4,127,902 | 12/1978 | Homsy | 623/13 |
| 4,411,027 | 10/1983 | Alexander et al. | 623/13 |
| 4,584,722 | 4/1986 | Levy et al. | 623/13 |
| 4,718,907 | 1/1988 | Karwoski et al. | 623/1 |
| 4,942,873 | 7/1990 | Hlavacek et al. | 606/230 |
| 5,007,926 | 4/1991 | Derbyshire | 623/1 |
| 5,282,848 | 2/1994 | Schmitt | 623/1 |
| 5,318,575 | 6/1994 | Chesterfield et al. | 623/13 |

FOREIGN PATENT DOCUMENTS 9011735  10/1990  WIPO .................................. 623/13

OTHER PUBLICATIONS

Amis et al., "Long-Term Tissue Reactions To Polyester Fibre Anterior Cruciate Ligament Reconstructions In Ovine And Humane Joints", *JBJS*, vol. 74–B Supp. III (1992).

Primary Examiner—Paul B. Prebilic
Attorney, Agent, or Firm—Cesari and McKenna

[57] ABSTRACT

A sterile, surgically implantable prosthetic device for replacement of fibrous connective tissue is disclosed. The invention includes a series of nonabsorbable longitudinal threads that accept longitudinal stresses, and a series of closely spaced, nonabsorbable lateral fibers that spread stresses experienced by various ones of the longitudinal threads to adjacent longitudinal threads. These components in combination substantially enhance durability, and allow the present invention to accommodate multicentered axes of rotation. The invention also preferably includes a bioabsorbable sheet disposed on one side of the nonabsorbable-fiber sheet. This sheet encourages tissue ingrowth and vascularization, and also establishes a barrier around the nonabsorbable components that protects surrounding tissue structures from abrasion and guards the nonabsorbable components against biological degradation.

18 Claims, 4 Drawing Sheets

PROSTHETIC DEVICE FOR REPAIR AND REPLACEMENT OF FIBROUS CONNECTIVE TISSUE

BACKGROUND OF THE INVENTION

1. Field of the Invention

The present invention relates to surgical implants, and in particular to a prosthetic device for replacing injured ligamentous structures.

2. Description of the Related Art

Fibrous connective tissues (e.g., ligaments and tendons) provide essential support and stability to the musculoskeletal system. Damage to or loss of these tissues can result in disabling permanent injury. Unfortunately, because of the large and repeated stresses to which they are subjected even by routine activity, their replacement or reconstruction is particularly problematic. Prostheses for fibrous connective tissues must not only retain functional integrity under heavy mechanical burdens, but also withstand the body's natural degradative processes while maintaining biological and physical compatibility with surrounding tissue; in addition, they should facilitate immediate joint motion following surgery and a minimal period of activity restriction. This highly demanding combination of requirements has heretofore limited the success of prostheses fabricated from synthetic material, and surgeons therefore often resort to autogenous tissue grafts for augmentation or replacement of damaged fibrous connective tissues. Prior artificial devices have either failed mechanically in situ or caused unintended damage to surrounding tissue by abrasive wear, fragmentation, debris formation, joint effusion, joint laxity, restricted joint motion, contraction and/or calcification.

An attempt to surmount these difficulties using a combination of absorbable and nonabsorbable prosthetic components is described in U.S. Pat. No. 4,942,875. This reference describes repair devices consisting of mixed fiber bundles woven, braided or knitted together. While such devices may offer biological compatibility with surrounding tissues, their necessarily rough surfaces have been known to cause substantial abrasion damage to surrounding tissues over time as a consequence of the patient's post-operative activity. Moreover, like other prior approaches, the '875 devices make no mechanical provision for the multicentric axes of rotation encountered anatomically. One immediate result is loss of joint motion; but over time, the mechanical stresses imposed by natural joint action can result in weakening and, ultimately, fragmentation and breakage of the prosthetic fibers, since these are designed to accommodate only longitudinal forces. Indeed, even purely longitudinal stresses can ultimately cause failure of such devices if localized to particular longitudinal fibers.

Finally, prior devices such as that disclosed in the '875 patent do not support significant vascular ingrowth or deep tissue permeation, particularly in the case of relatively thick prostheses. Such tissue growth is essential both to integration of a prosthesis within its surrounding tissue enviromnent, as well as to the regeneration of natural fibrous connective tissue to enhance the performance of the prosthesis itself.

DESCRIPTION OF THE INVENTION

OBJECTS OF THE INVENTION

Accordingly, it is an object of the present invention to provide prosthetic devices for replacement of fibrous connective tissue that optimally distribute local stresses across the device.

It is another object of the invention to achieve biological integration of implanted prosthetic devices through ingrowth of bone, connective and vascular tissue.

It is still another object of the invention to provide prosthetic replacements for connective tissue that encourage the natural growth of replacement tissue while functioning prosthetically.

Yet another object of the invention is to provide prosthetic replacements for connective tissue that diffuse stress across a series of parallel fibers adjacent the area of maximum stress.

It is yet another object of the present invention to provide ligament replacements that exhibit mechanical characteristics and durability comparable to the natural tissue.

It is a further object of the invention to provide prosthetic replacements for connective tissue that substitute for the lost tissue upon implantation and thereby permit immediate joint motion.

It is yet a further object of the invention to provide prosthetic replacements for connective tissue that accommodate multicentric axes of rotation.

Still another object of the invention to provide prosthetic replacements for connective tissue that do not damage surrounding tissue in situ.

Other objects will, in part, be obvious and will, in part, appear hereinafter. The invention accordingly comprises an article of manufacture possessing the features and properties exemplified in the constructions described herein and the several steps and the relation of one or more of such steps with respect to the others and the apparatus embodying the features of construction, combination of elements and the arrangement of parts that are adapted to effect such steps, all as exemplified in the following summary and detailed description, and the scope of the invention will be indicated in the claims.

BRIEF SUMMARY OF THE INVENTION

The foregoing objects are attained using a combination of components that collectively provide a sterile, surgically implantable prosthetic device for replacement of fibrous connective tissue, typically ligamentous structures. The invention includes integral means of in vivo placement and attachment to surrounding tissue structures, and exhibits strength equal to or exceeding that of the intact anatomic structure it replaces.

The prostheses of the present invention include a series of nonabsorbable longitudinal threads that accept longitudinal stresses, and a series of closely spaced, nonabsorbable lateral fibers that spread stresses experienced by various ones of the longitudinal threads to adjacent longitudinal threads. These components in combination substantially enhance durability, and allow the present invention to accommodate multicentered axes of rotation. The longitudinal fibers extend past opposed edges of the lateral fibers, which are arranged as a bounded sheet, and facilitate surgical attachment of the device.

The invention also preferably includes a bioabsorbable sheet disposed on one side of the nonabsorbable-fiber sheet. Unlike the fibers and threads, the bioabsorbable sheet is expressly intended to be degraded by the body following surgical implantation. This sheet encourages tissue ingrowth and vascularization, and also establishes a barrier around the nonabsorbable components that protects surrounding tissue structures from abrasion and guards the nonabsorbable components against biological degradation. The various components of the invention are most conveniently rolled into a tubular form for implantation.

BRIEF DESCRIPTION OF THE DRAWINGS

The foregoing discussion will be understood more readily from the following detailed description of the invention, when taken in conjunction with the accompanying drawings, in which.

DETAILED DESCRIPTION OF THE PREFERRED EMBODIMENTS

Figure 1:
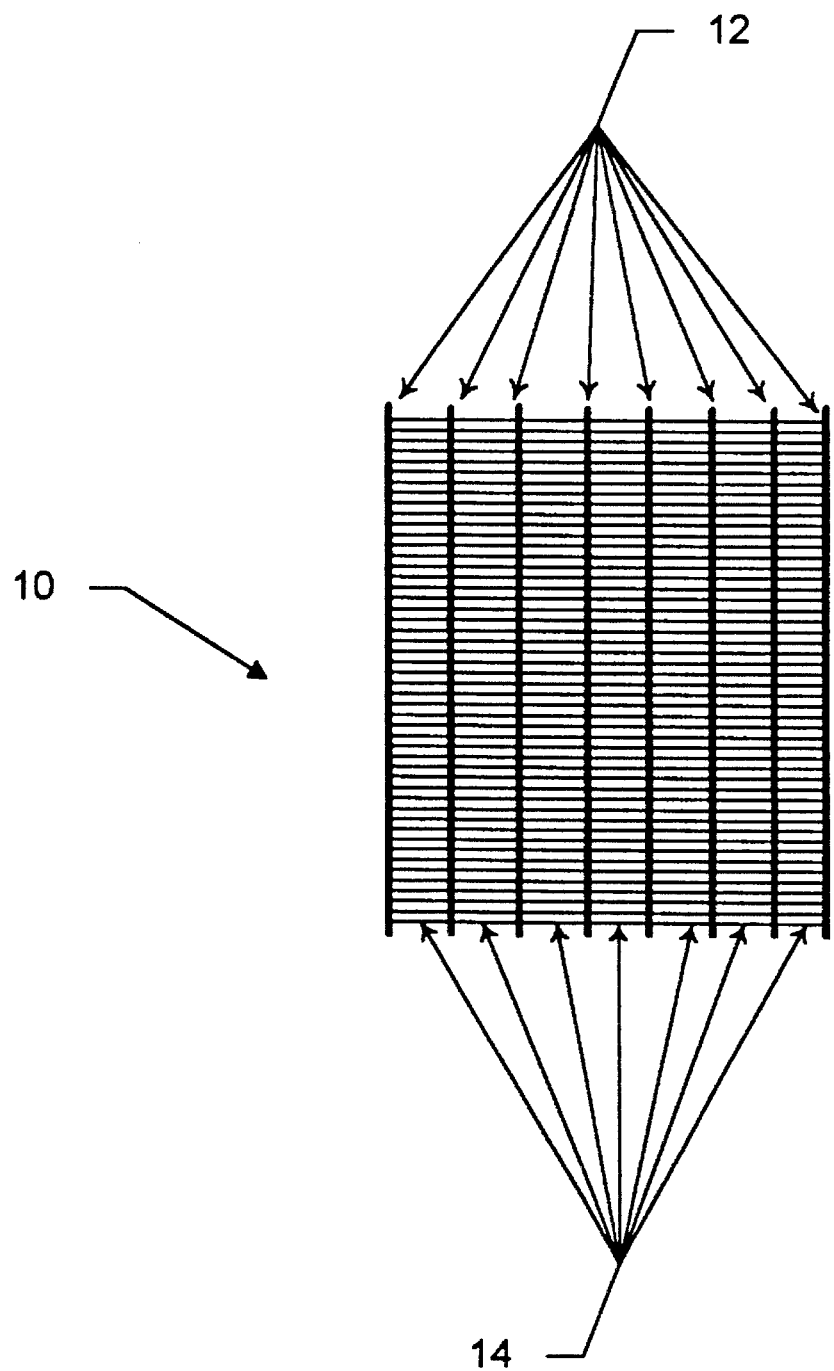
FIG. 1 is a plan view illustrating the basic components of the invention.

Refer first to FIG. 1, which illustrates the two primary components of the present invention, shown in the form of a bounded sheet 10. These include a series of longitudinal threads 12, fabricated from a high-strength material that resists biological degradation, and a web of closely spaced, nonabsorbable lateral fibers 14 through which threads 12 are interwoven. Fibers 14 spread stresses applied to various ones of threads 12 to adjacent threads. This is accomplished by spacing fibers 14 sufficiently close to one another that, when threads 12 are interwoven therethrough, a tight mesh is formed. Longitudinal forces applied along a particular thread 12 will then distort the adjacent lateral fibers 14, and this distortion is transmitted to adjacent threads 12 by virtue of their tight coupling to fibers 14. Accordingly, fibers 14 effectively connect the stressed thread 12 to all other threads, spreading the effect of forces applied unequally to particular threads. Fibers 14 also accept lateral forces along their lengths.

Figure 2B:
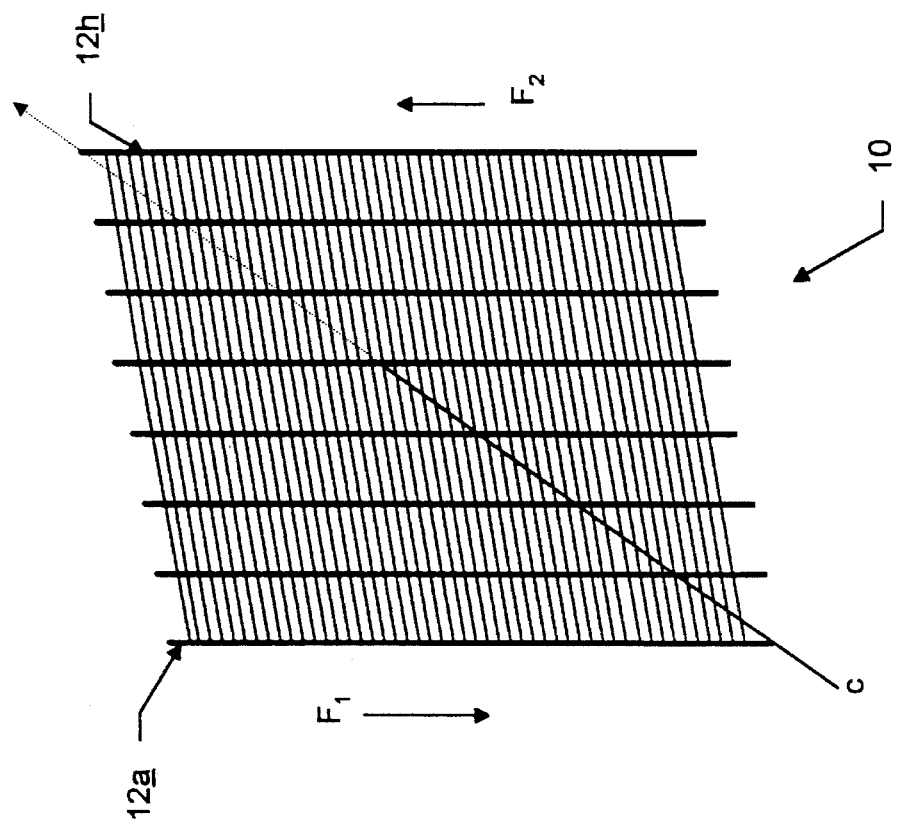
FIGS. 2A and 2B illustrate the response of the present invention to longitudinally applied forces.
Figure 2A:
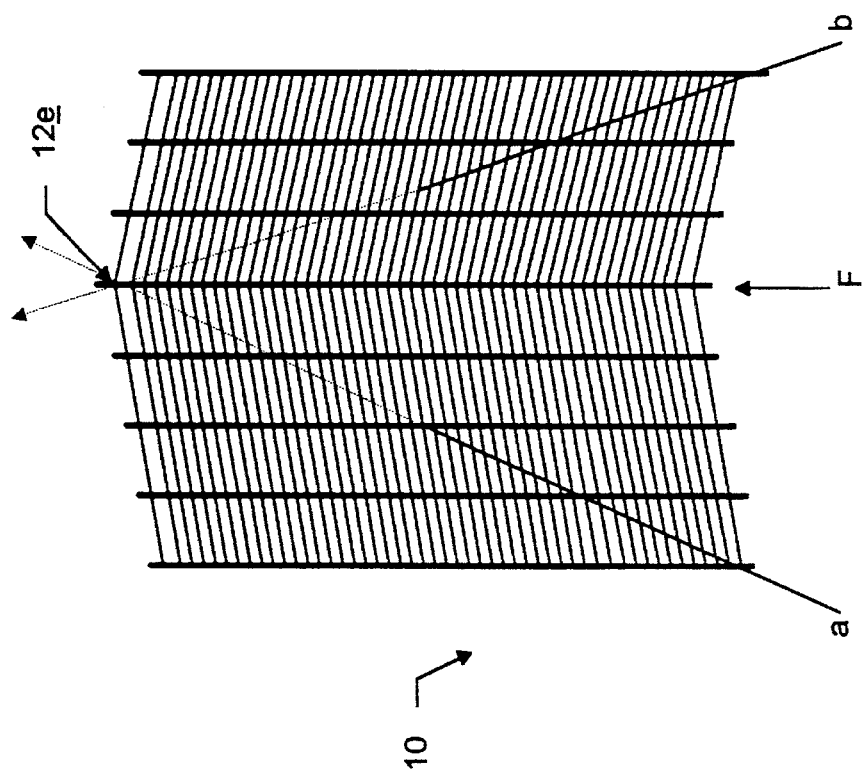

Through this mode of action, the present invention exhibits substantial durability as well as the ability to accommodate the multicentered axes of rotation traversed by healthy ligaments. This capability is illustrated in FIGS. 2A and 2B. In FIG. 2A, an upward force F applied to a single thread 12e results in torsion of the sheet 10 around two rotational axes a, b. The depicted torsion causes bulk movement of the entire sheet 10, rather than just the single thread 12e, along the direction of the force.

The device 10 also readily accommodates shearing forces, as illustrated in FIG. 2B. The parallel, opposed forces $F_1$, $F_2$ twist the entire sheet 10 around the single rotational axis c, rather than exerting independent and isolated effects on the end threads 12a, 12h.

The device of the present invention is capable, as soon as it is implanted in a patient, of bearing the normal stress loads experienced by the intact anatomic structure it has replaced, thereby permitting immediate joint motion and a relatively short post-operative recovery period. In addition, the invention also encourages and accommodates ingrowth of new ligamentous tissue. This function is provided by fibers 14, which serve as a base for ingrowth of collagen fibers and new vascular channels. As this natural healing process progresses, fibers 14 continue to spread longitudinal forces and accept lateral forces, but these functions are gradually shared with the growing fibrous tissue. If, as described below, fibers 14 are partially bioabsorbable, natural fibrous tissue assumes that portion of the load borne by the bioabsorbable material as it decays.

Figure 3:
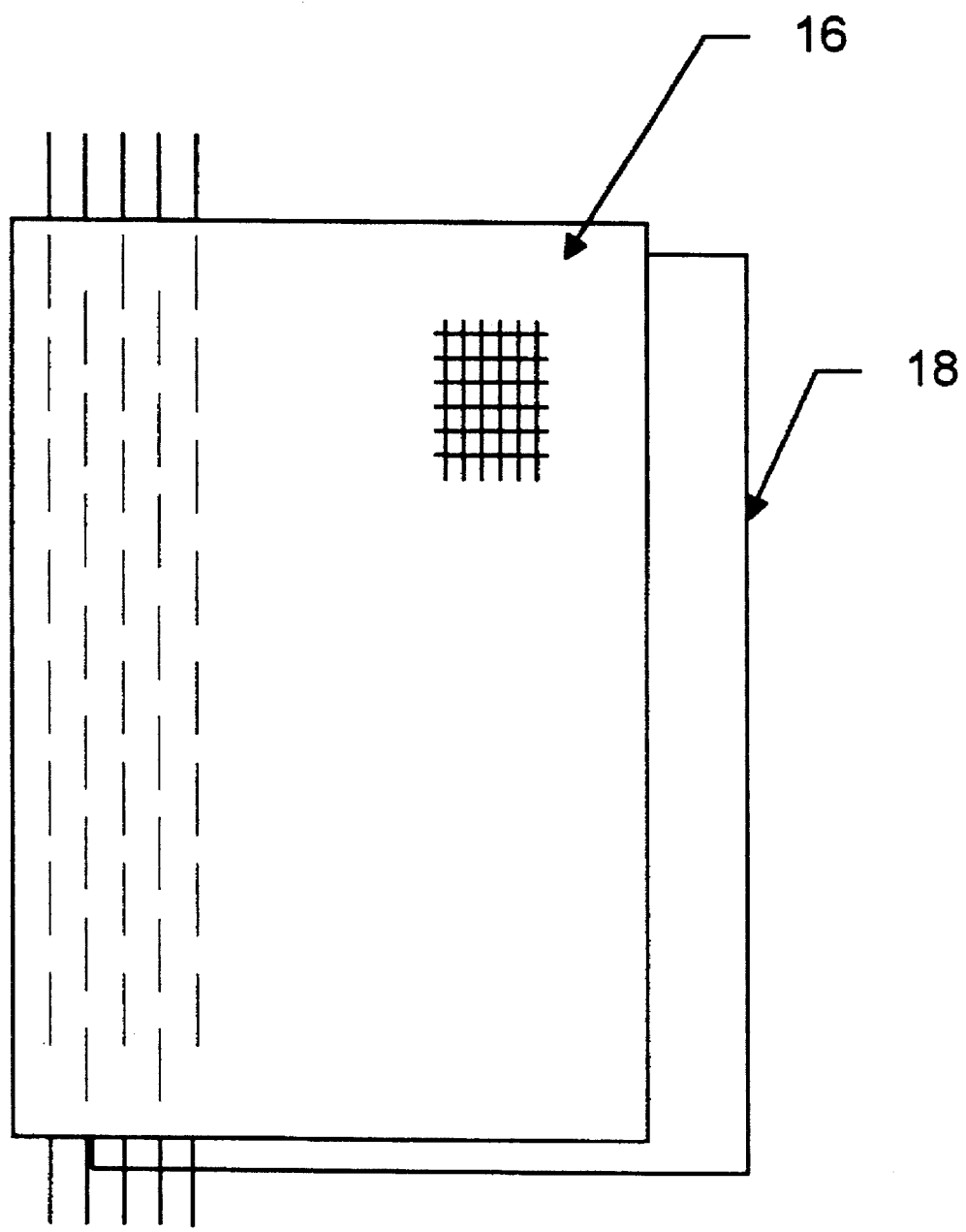
FIG. 3 is a plan view of a preferred embodiment of the invention, shown in sheet form.
Figure 4:
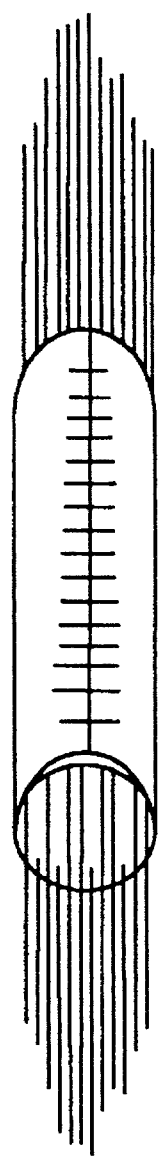
FIG. 4 is an isometric view of the components of the invention illustrated in FIG. 3, rolled into tubular form for surgical implantation.

In order to accommodate tissue ingrowth, the fibers 14 are spaced no closer than 300 µm apart. Beyond this minimum parameter, the spacing of fibers 14 is not critical, although the spacing cannot be so wide as to undermine the longitudinal force-spreading function. Fibers 12 and 14 can be fabricated from the same material, and are typically interwoven with a spacing between adjacent fibers 12 that exceeds the spacing between adjacent fibers 14. Furthermore, to simplify production, fibers 14 may be provided in the form of a rough-weave mesh, indicated at reference numeral 16 of FIG. 3, with threads 12 interwoven therethrough. In the ensuing discussion, sheet 16 will be referred to generically to denote a mesh, as shown in FIG. 3, or a web as shown in FIG. 1.

Both threads 12 and fibers 14 are preferably "nonabsorbable" in the sense of either exhibiting long-term resistance to biological degradation, or encouraging ingrowth of natural tissue and bioabsorbing, if at all, no faster than their load-bearing function can be assumed by such tissue. In either case, any exhibited bioabsorption does not lead to loss of function, and the term "nonabsorbable" is herein used to denote both types of material behavior.

An ideal material of the latter type is a precipitated collagen preparation that mimics the biological and mechanical characteristics of natural fibrous connective tissue and retains adequate tensile strength until the loads to which it is exposed in situ are assumed by natural tissue ingrowth. Such materials, while not yet available on a widespread basis, are known to those skilled in the art. See, e.g., Dunn et al., "Fibroblast-Seeded Collagen Scaffolds for ACL Reconstruction," *Transactions of the* 40th Annual Meeting of the Orthopedic Research Societyat page 36–7 (1994) (the disclosure of which is hereby incorporated by reference). Other suitable materials, in unidirectional web or bidirectional mesh form, include polyester, polyalkylene terephthalate, polyamide polyurethane, and polyether-polyester block copolymer. A suitable fiber mesh is the uncoated, braided DACRON polyester cloth used for conventional arterial grafts, in suture sizes ranging from No. 2-0 to 5-0, marketed by Medox Medical Corp. Fibers 14 may also be coated with a material that promotes tissue adhesion and ingrowth, e.g., a very thin layer of a bioabsorbable polymer such as polyglycolic acid, polydioxanone, trimethylene carbonate linkages, or copolymers or physical combinations thereof. Ordinarily, the ratio of longitudinal length to lateral width of sheets 16 and 18 will exceed 1.

Threads 12 are also ideally fabricated from precipitated collagen with the characteristics discussed above. Synthetic alternative materials must exhibit high tensile strength and long-term resistance to biological degradation. A useful material for threads 12 is braided polyester fiber having a uniform thickness equivalent to No. 2 surgical suture; indeed, No. 2 uncoated, braided DACRON polyester suture, such as that marketed by Ethicon Inc. or the Davis & Geck division of American Cyanamid Company is entirely suitable. Each thread 12 is woven through fibers 14 and generally extends 20 to 30 cm beyond opposed edges of sheet 16. The precise lateral spacing between fibers 14 is not critical; spacings of approximately 0.5 to 2 mm are easily obtained and have proven satisfactory. However, it is preferred that the stitches through fibers 14 alternate with respect to one another, as shown in FIG. 3.

It is also preferred to add a bioabsorbable cloth or mesh sheet 18 on one side of nonabsorbable sheet 16 so as to fully cover it. Sheet 18 should have dimensions that exceed those of nonabsorbable sheet 16 by approximately 1–2 mm on each side, and is fabricated from a bioabsorbable polymer such as polyglycolic acid, polydioxanone, trimethylene carbonate linkages, or copolymers or physical combinations thereof. The weave size of sheet 18 is comparable to or larger than that of cloth used for conventional arterial grafts.

Sheet 18 serves a number of functions, and these are especially apparent in the context of the invention in its most common implant form, namely, rolled into a tube with sheet 18 on the outside. The exposed edge 20 of sheet 18 is stitched into the body of the tube (e.g., by stitching threads 12 through both fibers 14 and sheet 18, preferably in the alternating pattern shown in FIG. 3). Sheet 18 thereby acts as a smooth, tissue-compatible surface that avoids the harsh abrasion characteristics of prior-art devices. Within hours of implantation, sheet 18 becomes covered with a fibrin clot that encourages the growth of a collagenous layer thereover, further protecting surrounding tissue and guarding the other components of the invention against external biological attack. Sheet 18 also facilitates deep vascularization and tissue penetration. As it decays, sheet 18 interacts with surrounding tissue, encouraging cell migration and vascularization into the underlying nonabsorbable sheet 16 (which is gradually exposed). The spiral channel between absorbable sheet 18 and nonabsorbable sheet 16 provides a further pathway for tissue ingrowth prior to substantial bioabsorption of sheet 18.

In order to further enhance cell migration and proliferation, vascularization, and collagen secretion, any or all of the components (i.e., threads 12, fibers 14 and/or sheet 18) may be coated with a natural tissue factor such as tissue fibroblast growth factor.

In practice, the device 10 is appropriately positioned within the patient's body, and threads 12 projecting from each end of the rolled device are stapled, sewn or otherwise attached to anchoring anatomic structures; for example, threads 12 may be threaded through a needle for soft-tissue attachment and knotting. A similar arrangement is advantageously used to guide the device through bone or soft-tissue tunnels. Absorbable surgical suture may be wound around the tubular structure in order to decrease its implantation diameter and/or to facilitate introduction through slender anatomic passages.

It will therefore be seen that the foregoing represents a versatile and highly reliable approach to prosthetic replacement of ligamentous structures. The terms and expressions employed herein are used as terms of description and not of limitation, and there is no intention, in the use of such terms and expressions, of excluding any equivalents of the features shown and described or portions thereof, but it is recognized that various modifications are possible within the scope of the invention claimed.

What is claimed is:

1. A replacement device for fibrous connective tissue, the device having a generally tubular form and comprising:
   a. a series of nonabsorbable lateral fibers arranged in parallel and spaced apart by a distance adequate to allow cellular ingrowth;
   b. a series of nonabsorbable longitudinal threads arranged in parallel and woven through the lateral fibers such that longitudinal force applied along various ones of the threads is partially transmitted, via the fibers, to adjacent threads, the adjacent longitudinal threads being spaced apart by a distance exceeding the distance between the adjacent lateral fibers and projecting beyond the lateral fibers for attachment to an anatomical structure.

2. The device of claim 1 wherein the lateral fibers are spaced at least 300 μm apart.

3. The device of claim 1 wherein the fibers form a bounded sheet and the threads extend beyond opposed edges of the sheet.

4. The device of claim 2 wherein the lateral fibers are interwoven with longitudinal threads that are identical to the lateral fibers to form a mesh in which the spacing between lateral fibers is at least 300 μm, and the longitudinal threads are interwoven into the mesh with a spacing between threads that exceeds the spacing between lateral fibers.

5. The device of claim 1 wherein adjacent longitudinal threads are woven through the lateral fibers in an alternating pattern.

6. The device of claim 3 further comprising a second, bioabsorbable sheet at least as large as the fiber sheet and disposed on a side thereof.

7. The device of claim 6 wherein the threads are interwoven through the fibers and through the absorbable sheet.

8. The device of claim 6 wherein the device is rolled into a tubular form.

9. The device of claim 8 wherein the tubular device forms a channel between the fibers and the absorbable sheet capable of receiving fibroblasts and vascular tissue.

10. The device of claim 3 wherein the sheet and the threads are fabricated from a synthetic polymer.

11. The device of claim 10 wherein the threads are braided polyester fibers.

12. The device of claim 10 wherein the mesh is coated with a thin layer of bioabsorbable polymer.

13. The device of claim 12 wherein the bioabsorbable polymer comprises at least one material from the group consisting of polyglycolic acid, polylactic acid, polydioxanone, and trimethylene carbonate.

14. The device of claim 1 wherein either the fibers or the threads are fabricated from precipitated collagen.

15. The device of claim 1 wherein both the fibers and the threads are fabricated from precipitated collagen.

16. The device of claim 5 wherein the sheet is fabricated from at least one material from the group consisting of polyglycolic acid, polylactic acid, polydioxanone, and trimethylene carbonate.

17. The device of claim 4 wherein the mesh has a length and a width, the threads being interwoven along the length of the mesh and the ratio of length to width being in excess of 1.

18. The device of claim 6 further comprising a coating of a natural tissue factor on at least one element selected from the group consisting of the fiber sheet, the bioabsorbable sheet and the threads.

* * * * *